(12) United States Patent
Akahori

(10) Patent No.: US 8,559,593 B2
(45) Date of Patent: Oct. 15, 2013

(54) RADIOGRAPHY APPARATUS INCLUDING A MODE SELECTION UNIT FOR SELECTING A TOMOSYNTHESIS MODE BASED ON REGION BEING RADIOGRAPHED

(75) Inventor: Sadato Akahori, Kanagawa-ken (JP)

(73) Assignee: FUJIFILM Corporation, Tokyo (JP)

(*) Notice: Subject to any disclaimer, the term of this patent is extended or adjusted under 35 U.S.C. 154(b) by 396 days.

(21) Appl. No.: 12/923,558

(22) Filed: Sep. 28, 2010

(65) Prior Publication Data
US 2011/0075795 A1    Mar. 31, 2011

(30) Foreign Application Priority Data

Sep. 28, 2009 (JP) ................................. 2009-222250

(51) Int. Cl.
*H05G 1/60* (2006.01)
*H05G 1/64* (2006.01)

(52) U.S. Cl.
USPC .................. 378/26; 378/22; 378/25; 378/115; 378/116; 378/196; 378/197

(58) Field of Classification Search
USPC ................ 378/21–27, 37, 115, 116, 196, 197
See application file for complete search history.

(56) References Cited

U.S. PATENT DOCUMENTS

| | | | | |
|---|---|---|---|---|
| 6,341,156 B1 * | 1/2002 | Baetz et al. | ................. | 378/98.8 |
| 6,411,674 B1 * | 6/2002 | Oikawa | ........................... | 378/21 |
| 6,901,132 B2 * | 5/2005 | Eberhard et al. | ............... | 378/23 |
| 6,914,958 B2 * | 7/2005 | Ganin | ............................ | 378/26 |
| 6,925,144 B2 * | 8/2005 | Matsumoto | .................... | 378/22 |
| 6,940,943 B2 * | 9/2005 | Claus et al. | .................... | 378/27 |
| 6,970,531 B2 | 11/2005 | Eberhard et al. | | |
| 6,973,160 B2 * | 12/2005 | Matsumoto | .................... | 378/22 |
| 7,123,683 B2 * | 10/2006 | Tsujii | ............................ | 378/26 |
| 7,313,219 B2 | 12/2007 | Endo | | |
| 7,778,388 B2 * | 8/2010 | Sendai | .......................... | 378/22 |
| 8,005,184 B2 * | 8/2011 | Chen | ................................ | 378/4 |
| 8,094,773 B2 * | 1/2012 | Boese et al. | ..................... | 378/9 |
| 8,184,765 B2 * | 5/2012 | Akahori | .......................... | 378/4 |
| 2003/0219101 A1 | 11/2003 | Tsujii | | |

FOREIGN PATENT DOCUMENTS

JP   2004-041702 A   12/2004

* cited by examiner

*Primary Examiner* — Allen C. Ho
(74) *Attorney, Agent, or Firm* — Jean C. Edwards, Esq.; Edwards Neils PLLC

(57) ABSTRACT

A radiation source and a detection means are moved relative to each other, thereby moving the radiation source to a plurality of positions. A subject is irradiated with radiation from the plurality of positions to obtain a plurality of radiographic images of the subject. A slice image of the subject is reconstructed from the plurality of radiographic images. At this time, a first mode for moving only the radiation source or a second mode for moving both of the radiation source and the detection means is selected based on the condition of radiography, and the plurality of radiographic images are obtained in the selected mode.

3 Claims, 7 Drawing Sheets

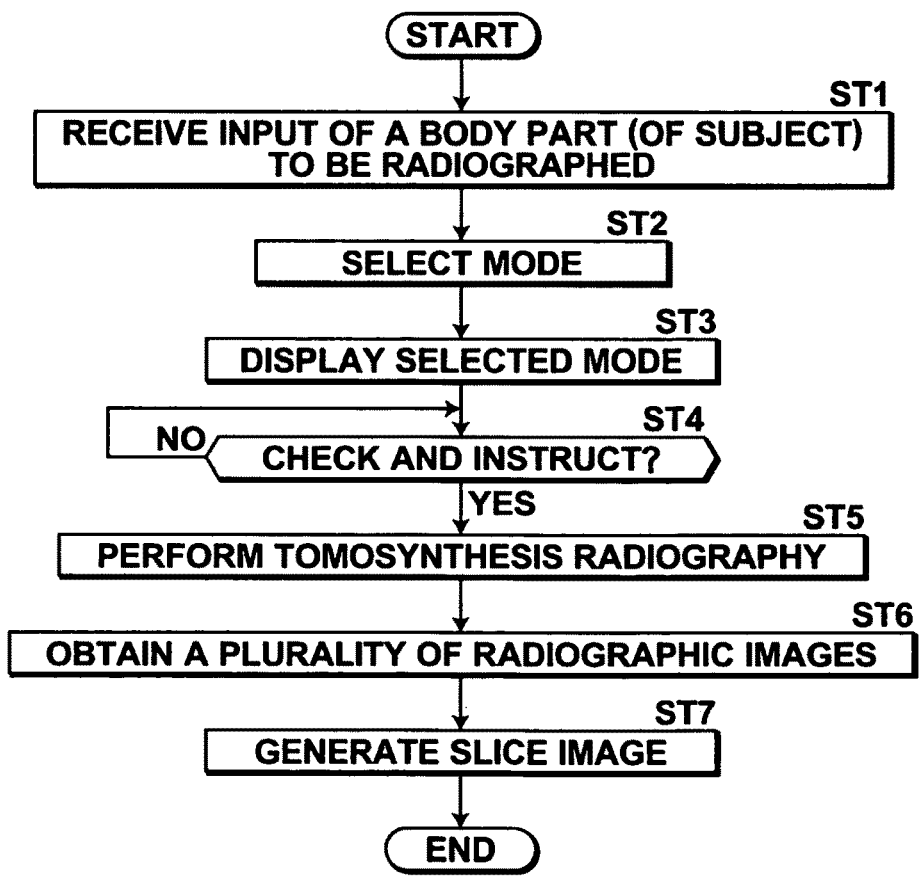

FIRST RADIOGRAPHY

SECOND RADIOGRAPHY

RADIOGRAPHY APPARATUS INCLUDING A MODE SELECTION UNIT FOR SELECTING A TOMOSYNTHESIS MODE BASED ON REGION BEING RADIOGRAPHED

CROSS-REFERENCE TO RELATED APPLICATIONS

The present application claims priority from Japanese Patent Application No. 2009-222250, filed Sep. 28, 2009, the contents of which are herein incorporated by reference in their entirety.

BACKGROUND OF THE INVENTION

1. Field of the Invention

The present invention relates to a radiography apparatus for performing tomosynthesis radiography to generate slice images of a subject.

2. Description of the Related Art

In recent years, tomosynthesis radiography was proposed to observe affected regions of patients in more detail by a radiography apparatus using X-rays. In tomosynthesis radiography, radiography is performed by moving an X-ray tube to different positions, and by irradiating a subject by the X-ray tube at different angles from the different positions. Further, images obtained by radiography are added to obtain an image in which a desired cross section of the subject is emphasized. In tomosynthesis radiography, the X-ray tube is moved parallel to an X-ray detector, or in such a manner to draw a circle or an ellipse or oval, based on the characteristic of a radiography apparatus and the kind of a slice image (tomogram) to be obtained. The subject is radiographed at different radiation angles to obtain a plurality of radiographic images, and a slice image of the subject is reconstructed from the plurality of radiographic images.

In tomosynthesis radiography, a system that can reduce a time period for obtaining a plurality of radiographic images has been proposed (please refer to U.S. Pat. No. 6,970,531 (Patent Document 1)). In the system, when a subject is irradiated with radiation, the X-ray tube is not stopped. Instead of stopping the X-ray tube, the movement speed of the X-ray is changed or the X-ray tube is continuously moved to reduce the time period for obtaining the plurality of radiographic images. Further, a system that obtains images of a plurality of cross sections of a subject in one radiography operation has been proposed (please refer to U.S. Pat. No. 7,313,219 (Patent Document 2)).

In tomosynthesis radiography, radiographic images are obtained by moving only the X-ray tube, or by moving both of the X-ray tube and the X-ray detector. To increase the size of a region in which slice images are reconstructable from a plurality of radiographic images, it is desirable that both of the X-ray tube and the X-ray detector are moved. However, when both of the X-ray tube and the X-ray detector are moved, if the X-ray detector is not moved accurately, the position of an object (target) projected onto a radiographic image shifts or the like, and there is a problem that the quality of a reconstructed slice image drops. In contrast, when only the X-ray tube is moved, the problem caused by the movement of the X-ray detector does not arises. Therefore, it is possible to reconstruct a slice image the quality of which is higher than that of a slice image obtained by moving both of the X-ray tube and the X-ray detector.

As described above, tomosynthesis radiography is performed by moving only the X-ray tube, or by moving both of the X-ray tube and the X-ray detector. Especially, the system disclosed in Patent Document 1 can optionally move the X-ray detector. Therefore, in the system of Patent Document 1, an operator (a radiographer) can select a mode in which the X-ray detector is not moved or a mode in which the X-ray detector is moved based on the condition of radiography, such as the purpose of radiography for obtaining a slice image and the size of a region of interest (ROI).

However, in the system disclosed in Patent Document 1, the operator needs to select whether only the X-ray tube is moved, or both of the X-ray tube and the X-ray detector are moved. Therefore, if the operator selects a mode that is not appropriate for the condition of radiography, it becomes impossible to obtain an image of desirable quality and a slice image including the region of interest. At this time, the operator may check a mode that is appropriate for the condition of radiography before selecting the mode. However, such operation of checking the mode every time of radiography imposes a heavy burden on the operator.

SUMMARY OF THE INVENTION

In view of the foregoing circumstances, it is an object of the present invention to make it possible to obtain an appropriate slice image based on the condition of radiography in tomosynthesis radiography without imposing a heavy burden on an operator.

A radiography apparatus of the present invention is a radiography apparatus comprising:

a radiation source that outputs radiation to a subject;

a detection means that detects the radiation that has passed through the subject;

an image obtainment means that moves the radiation source and the detection means relative to each other, thereby moving the radiation source to a plurality of positions, and that obtains a plurality of radiographic images of the subject by irradiating the subject with radiation from the plurality of positions;

an image reconstruction means that generates a slice image of the subject by reconstructing the plurality of radiographic images; and a selection means that selects, based on the condition of radiography, a first mode in which only the radiation source is moved or a second mode in which both of the radiation source and the detection means are moved when the plurality of radiographic images are obtained, wherein the image obtainment means obtains the plurality of radiographic images in the mode selected by the selection means.

The term "condition of radiography" represents a condition as a basis for selecting the first mode or the second mode. Specifically, a body part of a subject to be radiographed or a region of interest of the subject may be used as the condition of radiography. The condition of radiography is not limited to the body part of the subject to be radiographed nor to the region of interest of the subject. Alternatively, the purpose of examination using slice images (further examination or specific examination, ordinary examination, observation of the course of a disease, or the like), the kind of a lesion to be observed (calcification, a tumor, or the like), or the like may be used as the condition of radiography. Further, the term "region of interest" represents a region in which the degree of interest is particularly high in diagnosis using images, and which is a target of obtainment of a slice image in the subject. In the present invention, the region of interest is a three-dimensional region defined by a range in the depth direction of the subject (in other words, the direction in which radiation propagates) and a range in an in-plane direction of the subject, which is perpendicular to the depth direction.

The radiography apparatus of the present invention may further include a body part setting means that sets a body part of the subject to be radiographed. Further, the selection means may select the first mode or the second mode based on the set body part.

The radiography apparatus of the present invention may further include a region-of-interest setting means that sets a region of interest in the subject. Further, the selection means may select the first mode or the second mode based on the set region of interest.

In the radiography apparatus of the present invention, the radiation source and the detection means may be moved relative to each other in such a manner to be synchronized with each other in the second mode.

In the radiography apparatus, the second mode may be a mode in which the detection means is moved to a plurality of positions, and only the radiation source is moved while the detection means is located at each of the plurality of positions.

According to the present invention, the first mode in which only the radiation source is moved or the second mode in which both of the radiation source and the detection means are moved is selected based on the condition of radiography. Therefore, it is possible to select the first mode or the second mode so that an appropriate slice image is obtained based on the condition of radiography without imposing a heavy burden on an operator.

Further, when the first mode or the second mode is selected based on the body part of the subject to be radiographed, it is possible to select the first mode or the second mode so that a slice image appropriate for the body part to be radiographed is generated.

Further, when the first mode or the second mode is selected based on the region of interest, it is possible to select the first mode or the second mode so that an appropriate slice image including the region of interest is generated.

When the radiation source and the detection means are moved relative to each other in such a manner to be synchronized with each other in the second mode, it is possible to increase the size of a reconstructable region in the second mode, compared with the first mode.

In the second mode, when the detection means is moved to a plurality of positions, and only the radiation source is moved while the detection means is located at each of the plurality of positions, it is possible to further increase the size of a reconstructable region, compared with the case of moving the radiation source and the detection means relative to each other in such a manner to be synchronized with each other.

BRIEF DESCRIPTION OF THE DRAWINGS

FIG. 6 is a table showing correspondence between body parts to be radiographed and modes;

FIG. 7 is a flow chart of a process performed in the first embodiment;

DESCRIPTION OF THE PREFERRED EMBODIMENTS

Figure 1:
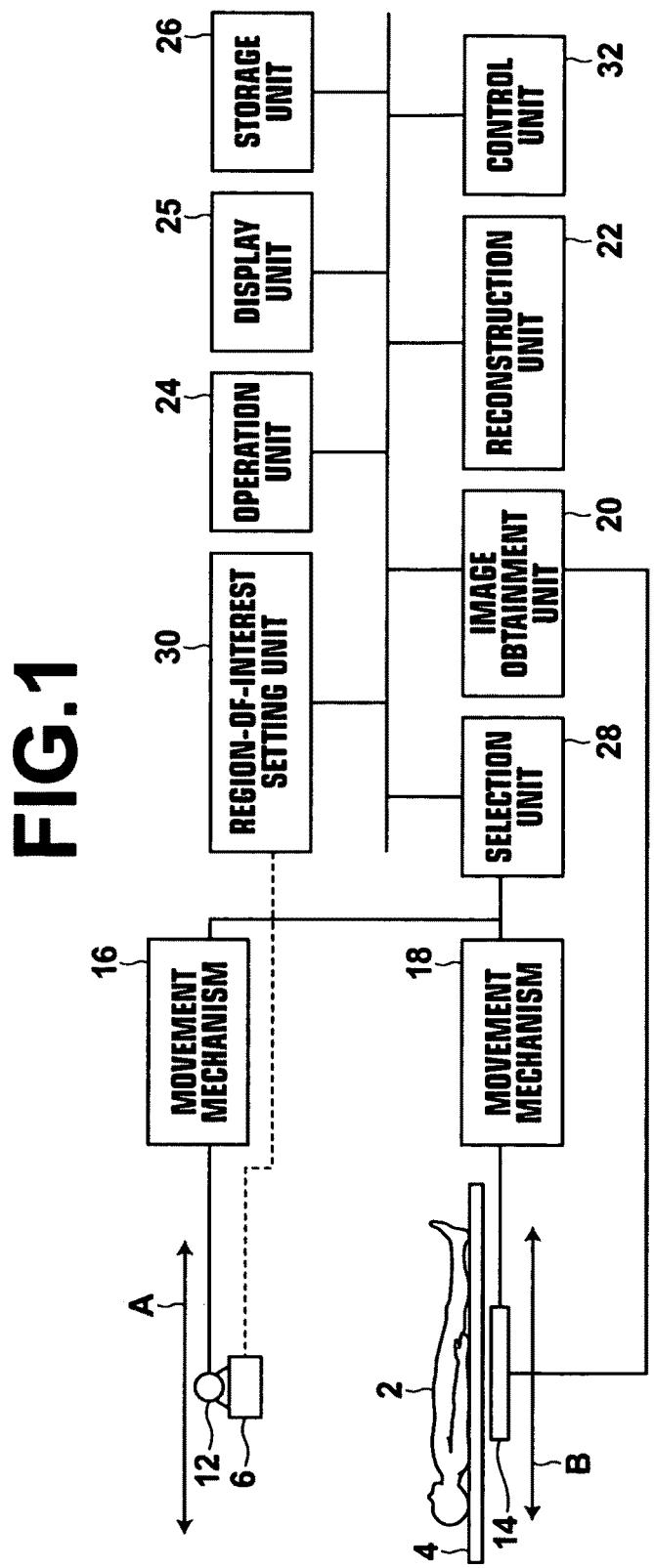
FIG. 1 is a schematic diagram illustrating the configuration of an X-ray radiography apparatus to which a radiography apparatus according to a first embodiment of the present invention has been applied.

Hereinafter, embodiments of the present invention will be described with reference to drawings. FIG. 1 is a schematic diagram illustrating an X-ray radiography apparatus to which a radiography apparatus according to a first embodiment of the present invention has been applied. As illustrated in FIG. 1, an X-ray radiography apparatus 10 according to the present embodiment includes an X-ray tube 12 and a flat-panel X-ray detector (hereinafter, simply referred to as a detector) 14. The X-ray tube 12 is moved straight or along an arc or curve by a movement mechanism 16. The X-ray tube 12 outputs, at a plurality of positions on the movement path thereof, X-rays to a subject 2 on the top board 4 of a radiographic table. In the present embodiment, it is assumed that the X-ray tube 12 moves along a straight line in the direction of arrow A. The dose of radiation of X-rays output to the subject 2 is controlled by a control unit, which will be described later, so that the dose of radiation becomes a predetermined value. Further, a collimator (a diaphragm for changing an irradiation field size) 6 is connected to the X-ray tube 12 so that an operator can set the range of the subject 2 irradiated with radiation.

The detector 14 is arranged in such a manner to face the X-ray tube 12 with the top board 4 of the radiographic table, on which the subject 2 is placed, therebetween. The detector 14 is arranged so as to detect X-rays that have passed through the subject 2. The detector 14 is moved straight or in an arc or curve as necessary by a movement mechanism 18, and detects X-rays that have passed through the subject 2 at a plurality of positions on the movement path of the detector 14. In the present embodiment, it is assumed that the detector 14 is moved in the direction of arrow B along a straight line.

The X-ray radiography apparatus 10 includes an image obtainment unit 20 and a reconstruction unit 22. The image obtainment unit 20 moves the X-ray tube 12 along a straight line, and obtains a plurality of radiographic images of the subject 2 by irradiating the subject 2 with X-rays from different angles by the X-ray tube 12 located at a plurality of positions in the movement path of the X-ray tube 12, and by detecting X-rays that have passed through the subject 2 by the detector 14. The reconstruction unit 22 reconstructs a slice image representing a desired cross section of the subject 2 from the plurality of radiographic images obtained by the image obtainment unit 20. The method for reconstructing a slice image will be described.

Figure 2:
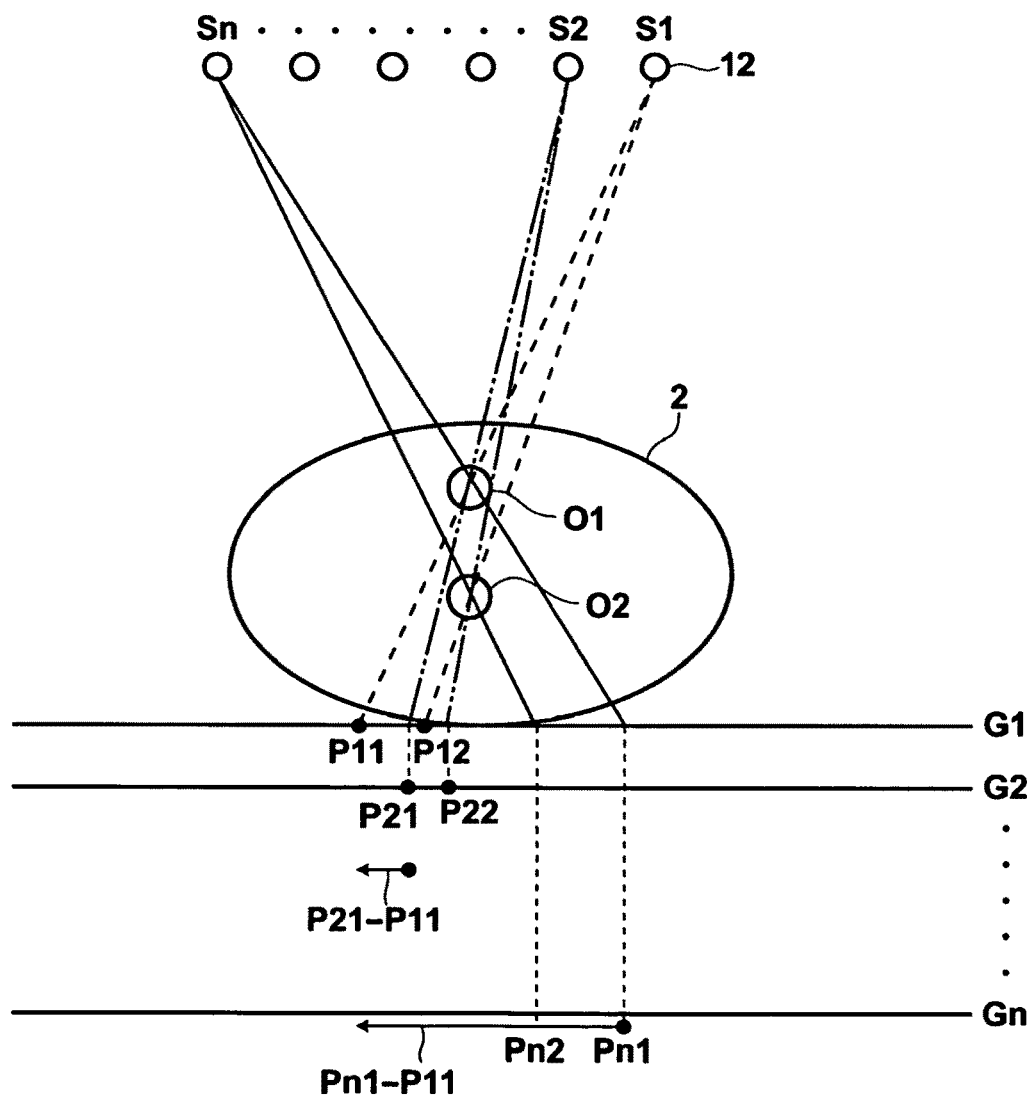
FIG. 2 is a diagram for explaining tomosynthesis radiography.

As illustrated in FIG. 2, when the X-ray tube 12 is moved to each position S1, S2, ..., Sn, and radiography is performed on the subject 2 from different irradiation angles, it is assumed that radiographic images G1, G2, ..., Gn are obtained when the X-ray tube 12 is located at positions S1, S2, ..., Sn, respectively. For example, when objects (O1, O2), which are located at different depths from each other, are projected from position S1, at which the X-ray tube 12 is located, the objects (O1, O2) are projected to positions P11 and P12 in the radiographic image G1, respectively. Further, when the objects (O1, O2) are projected from position S2, at which the X-ray tube 12 is located, the objects (O1, O2) are projected to positions P21 and P22 in the radiographic image G2, respectively. In this way, when projection of the objects (O1, O2) is repeated from different positions S1, S2, ..., Sn, at which the X-ray tube 12 is located, object O1 is projected to positions P11, P21, ..., Pn1, respectively, and object O2 is projected to positions P12, P22, ..., Pn2, respectively, in such a manner to correspond to the positions of the radiation source (X-ray tube 12).

When the cross section on which the object O1 is present should be emphasized, the radiographic image G2 is moved by P21-P11, the radiographic image G3 is moved by P31-P11, ..., the radiographic image Gn is moved by Pn1-P11, and the moved radiographic images are added to generate a slice image in which a structure on the cross section at the depth of the object O1 is emphasized. Further, when the cross section on which the object O2 is present should be emphasized, the radiographic image G2 is moved by P22-P12, the radiographic image G3 is moved by P32-P12, ..., the radiographic image Gn is moved by Pn2-P12, and the moved radiographic images are added. As described above, it is possible to obtain an image in which a slice image at a desired position is emphasized by matching the positions of the radiographic images G1, G2, ..., Gn based on the position of a necessary slice plane and by adding the radiographic images G1, G2, ..., Gn.

Further, the X-ray radiography apparatus 10 includes an operation unit 24, a display unit 25 and a storage unit 26. The operation unit 24 includes an input device, such as a keyboard, a mouse and a touch-panel-type device, and receives an instruction (information) for operating the X-ray radiography apparatus from an operator. In the present embodiment, each unit of the X-ray radiography apparatus 10 operates based on the information input by the operator at the operation unit 24. The display unit 25 is a display device, such as a liquid crystal monitor. The display unit 25 displays a radiographic image obtained by the image obtainment unit 20, and a slice image reconstructed by the reconstruction unit 22. Further, the display unit 25 displays a message necessary for the operation, and the like. The storage unit 26 stores various parameters, tables, or the like that are necessary to operate the X-ray radiography apparatus 10.

Further, the X-ray radiography apparatus 10 includes a selection unit 28. When a plurality of radiographic images are obtained in tomosynthesis radiography, the selection unit 28 selects a first mode or a second mode. In the first mode, only the X-ray tube 12 is moved, and in the second mode, both of the X-ray tube 12 and the detector 14 are moved in such a manner to be synchronized with each other. The selection unit 28 drives the movement mechanism 16 based on the result of selection. Further, the selection unit 28 optionally drives the movement mechanism 18 based on the selection result.

Figure 3:
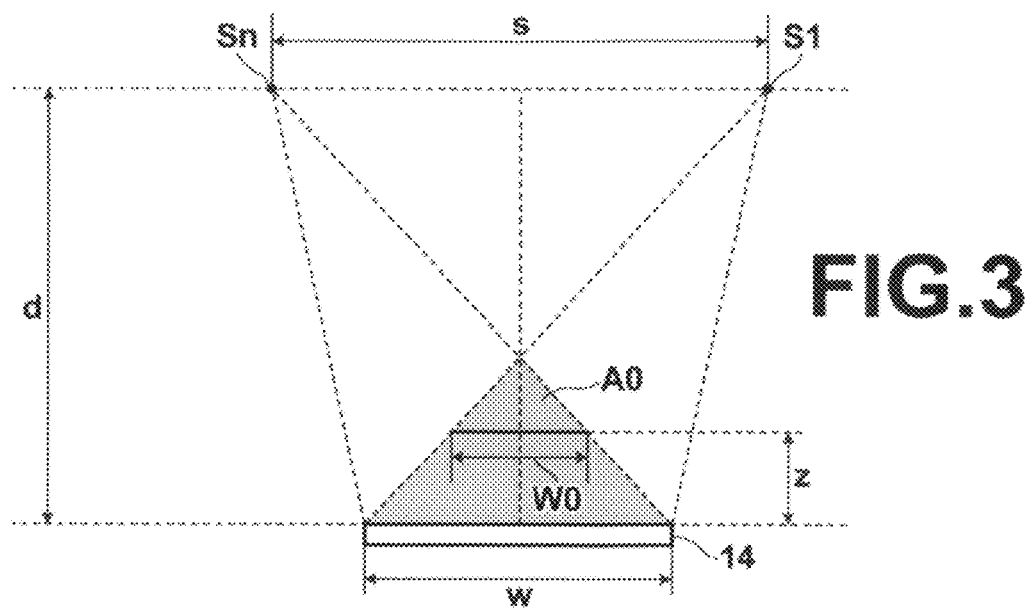
FIG. 3 is a diagram for explaining a reconstructable region in a first mode.
Figure 4:
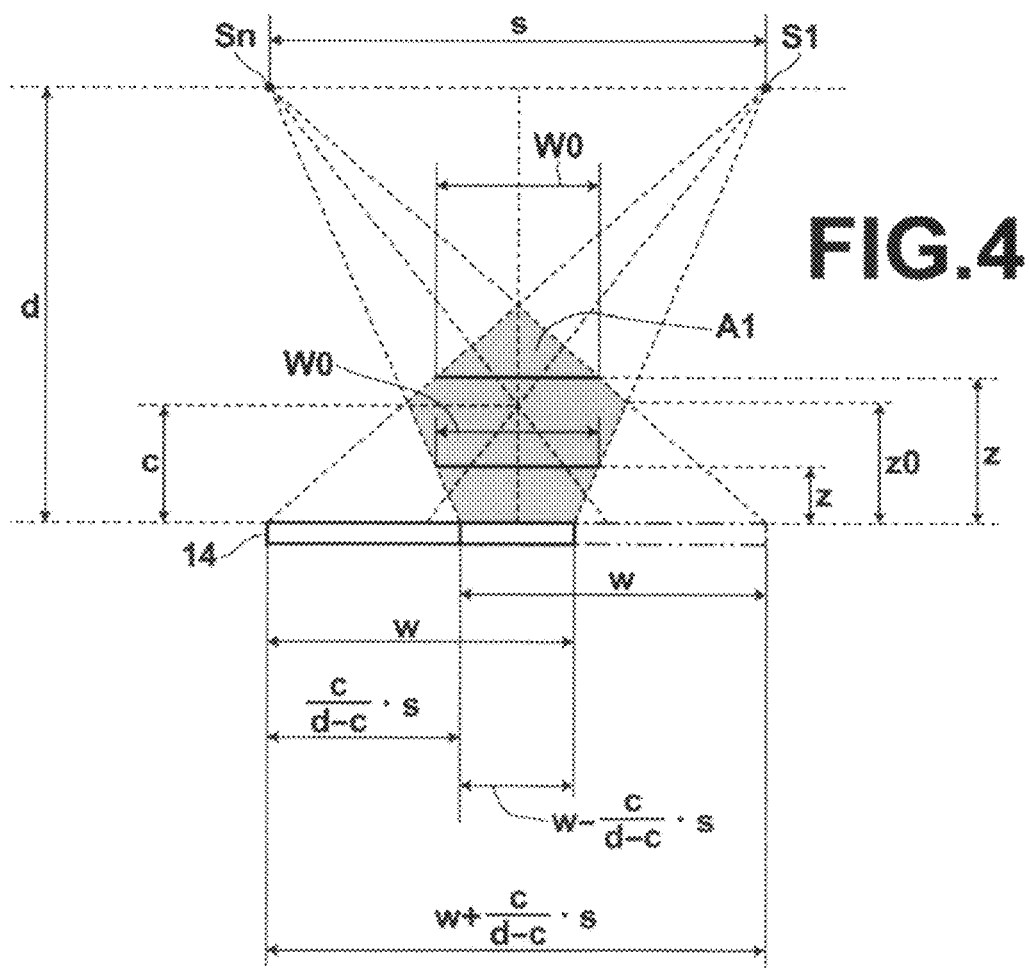
FIG. 4 is a diagram for explaining a reconstructable region in a second mode.

Next, a reconstructable region in the first mode and a reconstructable region in the second mode will be described. FIG. 3 is a diagram for explaining the reconstructable region in the first mode. FIG. 4 is a diagram for explaining the reconstructable region in the second mode. In FIGS. 3 and 4, only positions to which the X-ray tube 12 are moved are illustrated, and the X-ray tube 12 itself is not illustrated. Further, in FIGS. 3 and 4, the width of movement of the X-ray tube (a distance between position S1 and position Sn) is represented by s, a distance between the X-ray tube 12 and the detection surface of the detector 14 is represented by d, and the width of the detector 14 in the direction of movement of the X-ray tube is represented by w.

First, the case of the first mode will be described. As illustrated in FIG. 3, a reconstructable region, in which slice images can be reconstructed, is portion A0 (indicated in gray). In the portion A0, the range of irradiating the detector 14 with X-rays when the X-ray tube 12 is located at position S1 and the range of irradiating the detector 14 with X-rays when the X-ray tube 12 is located at position Sn overlap with each other. Here, the width W0 of the reconstructable region at arbitrary height z from the detection surface of the detector 14 may be calculated by using the following formula (1):

$$W0 = w - (w+s) \cdot z/d \quad (1).$$

In contrast, in the second mode, the detector 14 also moves. Therefore, as illustrated in FIG. 4, a reconstructable region, in which slice images can be reconstructed, is portion A1 (indicated in gray). In the portion A1, the range of irradiating the detector 14 with X-rays when the X-ray tube 12 is located at position 51 and the detector 14 is located at the farthest position from the X-ray tube 12 at 51 (the detector 14 is indicated by a solid line), and the range of irradiating the detector 14 with X-rays when the X-ray tube 12 is located at position Sn and the detector 14 is located at the farthest position from the X-ray tube 12 at Sn (the detector 14 is indicated by an imaginary line) overlap with each other. In FIG. 4, when the X-ray tube 12 is located at position 51, if a segment connects the X-ray tube 12 at S1 and the center of the width of the detector 14 located at the farthest position from the X-ray tube 12, and when the X-ray tube 12 is located at position Sn, if a segment connects the X-ray tube 12 at Sn and the center of the width of the detector 14 located at the farthest position from the X-ray tube 12, a distance from the intersection of the two segments to the detection surface of the detector 14 is distance c.

In FIG. 4, a distance between the left edge of the detector 14 when the detector 14 is located at the leftmost side (indicated by a solid line) and the left edge of the detector 14 when the detector 14 is located at the rightmost side (indicated by an imaginary line) is $c/(d-c) \cdot s$. Therefore, a distance between the right edge of the detector 14 when the detector 14 is located at the leftmost side and the left edge of the detector 14 when the detector 14 is located at the rightmost side is $w - c/(d-c) \cdot s$. Further, a distance between the left edge of the detector 14 when the detector 14 is located at the leftmost side and the right edge of the detector 14 when the detector 14 is located at the rightmost side is $w + c/(d-c) \cdot s$.

Here, width W0 of the region of interest at arbitrary height z from the detection surface of the detector 14 in the second mode may be calculated by using the following formulas (2) and (3). In formulas (2) and (3), a distance between a position at which the area of the reconstructable region becomes the largest and the detection surface of the detector 14 is represented by z0.

$$W0 = (w - c/(d-c) \cdot s) - (w - d/(d-c) \cdot s) \cdot z/d, \, (0 \le z \le z0) \quad (2)$$

$$W0 = (w + c/(d-c) \cdot s) - (w + d/(d-c) \cdot s) \cdot z/d, \, (z > z0) \quad (3)$$

Figure 5:
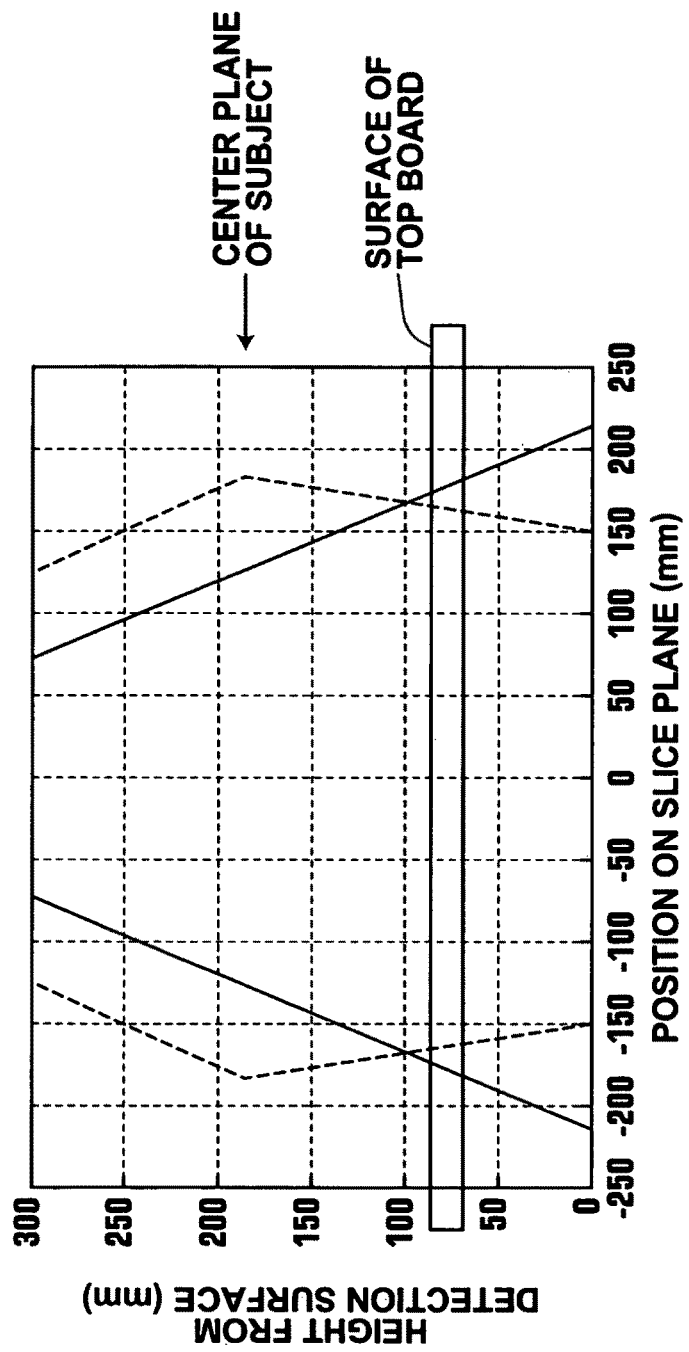
FIG. 5 is a diagram illustrating the result of comparison between the reconstructable region in the first mode and the reconstructable region in the second mode.

FIG. 5 is a diagram illustrating the result of comparison between the reconstructable region in the first mode and the recontructable region in the second mode. In FIG. 5, the outer edge of the reconstructable region in the first mode is illustrated by solid lines, and the outer edge of the reconstructable region in the second mode is illustrated by broken lines. When conditions, such as the method for moving the X-ray tube 12 and a distance between the X-ray tube 12 and the detection surface of the detector 14, differ from each other in the first mode and the second mode, the reconstructable region differs. Therefore, in the example illustrated in FIG. 5, it is assumed that the conditions are not changed in the first and second modes.

When FIGS. 3 and 4 are compared with each other, the reconstructable region in the first mode is larger than the reconstructable region in the second mode in the vicinity of the detection surface of the detector 14. However, since the top board 4 of the radiographic table is present on the upper side of the detector 14, an actually reconstructable region in the first mode is smaller by an amount corresponding to a distance between the detection surface of the detector 14 and the top board 4 of the radiographic table. Therefore, when the first mode and the second mode are compared with each other, the reconstructable region in the second mode is larger than the reconstructable region in the first mode in the vicinity of the center plane of the subject, as illustrated in FIG. 5.

In the first embodiment, the selection unit 28 selects the first mode or the second mode based on a body part to be radiographed that has been input by an operator at the operation unit 24. In the first embodiment, the storage unit 28 stores a table showing correspondence between body parts to be radiographed and modes. FIG. 6 illustrates a table showing correspondence between body parts to be radiographed and modes. As illustrated in FIG. 6, table T1 shows correspondence between an arm or leg, a head, a chest (breast) and an abdomen, which are examples of body parts to be radiographed, and modes (first mode or second mode) respectively.

The width of the arm or leg and the width of the head are narrower than the width of the chest and the width of the abdomen. Further, in images of the arm or leg and images of heads, the state of bones, the condition of blood vessels in the brain, and the like need to be clearly recognized. Therefore, the arm or leg and the head are linked to the first mode. In the first mode, the range of the reconstructable region is small, but a high quality slice image can be obtained. In contrast, the areas of the chest and the abdomen are larger than the area of the arm or leg or the area of the head. Therefore, the chest and the abdomen are linked to the second mode. In the second mode, the range of the reconstructable region is larger than the area of the reconstructable region in the first mode.

Further, the X-ray radiography apparatus 10 includes a region-of-interest setting unit 30. The operator sets the range of the subject 2 with respect to the depth direction (for example, a height from the top board of the radiographic table) by using the operation unit 24. Further, the operator sets the range of the subject 2 with respect to the in-plane direction, which is perpendicular to the depth direction, by using the collimator 6. When the operator sets the range by using the collimator 6, the subject 2 is illuminated with a beam of visible light through the collimator 6 instead of being irradiated with X-rays. Accordingly, the operator can set the range of the subject 2 with respect to the in-plane direction, which is perpendicular to the depth direction, by adjusting the range of visible light illuminating the subject 2. The region-of-interest setting unit 30 sets a three-dimensional region of interest based on the range of the subject 2 with respect to the depth direction, which has been set by the operator by using the operation unit 24, and the range of the subject with respect to the in-plane direction, which is perpendicular to the depth direction, the range being set by the operator by using the collimator 6.

Further, the X-ray radiography apparatus 10 includes a control unit 32 for controlling each unit of the X-ray radiography apparatus 10. The control unit 32 controls each unit of the X-ray radiography apparatus 10 based on an instruction from the operation unit 24.

Next, processing performed in the first embodiment will be described. FIG. 7 is a flow chart illustrating the process performed in the first embodiment. First, the control unit 32 receives an input of a body part to be radiographed by an operator from the operation unit 24 (step ST1). The selection unit 28 refers to table T1, which is stored in the storage unit 26, and selects the first mode or the second mode (mode selection, step ST2). Meanwhile, the control unit 32 displays the selected mode on the display unit 25 (step ST3) to make the operator check the selected mode. Further, the control unit 32 starts monitoring whether the operator has checked and instructed the mode (step ST4). If step ST4 is YES, tomosynthesis radiography is performed in the selected mode (step ST5), and the image obtainment unit 20 obtains a plurality of radiographic images (step ST6). Further, the reconstruction unit 22 reconstructs a slice image from the plurality of radiographic images (step ST7), and processing ends. The generated slice image is stored in a storage device, such as an HDD (hard disk drive), which is not illustrated. Alternatively, the generated slice image is sent to an external server through a network.

As described above, in the first embodiment, the first mode or the second mode is selected based on a body part to be radiographed. In the first mode, only the X-ray tube 12 is moved, and in the second mode, both of the X-ray tube 12 and the detector 14 are moved. In the first embodiment, it is possible to select the first mode or the second mode based on the body part to be radiographed so that an appropriate slice image is obtained without imposing any burden on the operator.

Next, a second embodiment of the present invention will be described. An X-ray radiography apparatus in the second embodiment of the present invention is structured in the same manner as the X-ray radiography apparatus 10 according to the first embodiment, and only the processing performed in the apparatus of the second embodiment differs from the processing performed in the apparatus of the first embodiment. Therefore, detailed descriptions on the structure of the X-ray radiography apparatus of the second embodiment are omitted. The X-ray radiography apparatus 10 of the second embodiment differs from that of the first embodiment, in that the selection of the first mode or the second mode is based on the region of interest in the X-ray radiography apparatus 10 of the second embodiment. Therefore, in the second embodiment, the selection unit 28 selects the first mode or the second mode based on the region of interest set by the region-of-interest setting unit 30. Further, the selection unit 28 drives the movement mechanism 16 based on the selection result. The selection unit 28 optionally drives the movement mechanism 18 based on the selection result.

In the second embodiment, the selection unit 28 compares the region of interest that has been set by the region-of-interest setting unit 30 with the reconstructable region in the first mode. If the region of interest that has been set by the region-of-interest setting unit 30 is included in the reconstructable region in the first mode, the selection unit 28 selects the first mode. However, if the region of interest that has been set by the region-of-interest setting unit 30 is not included in the reconstructable region in the first mode, in other words, if the set region of interest is larger than the reconstructable region in the first mode, the selection unit 28 selects the second mode.

Figure 8:
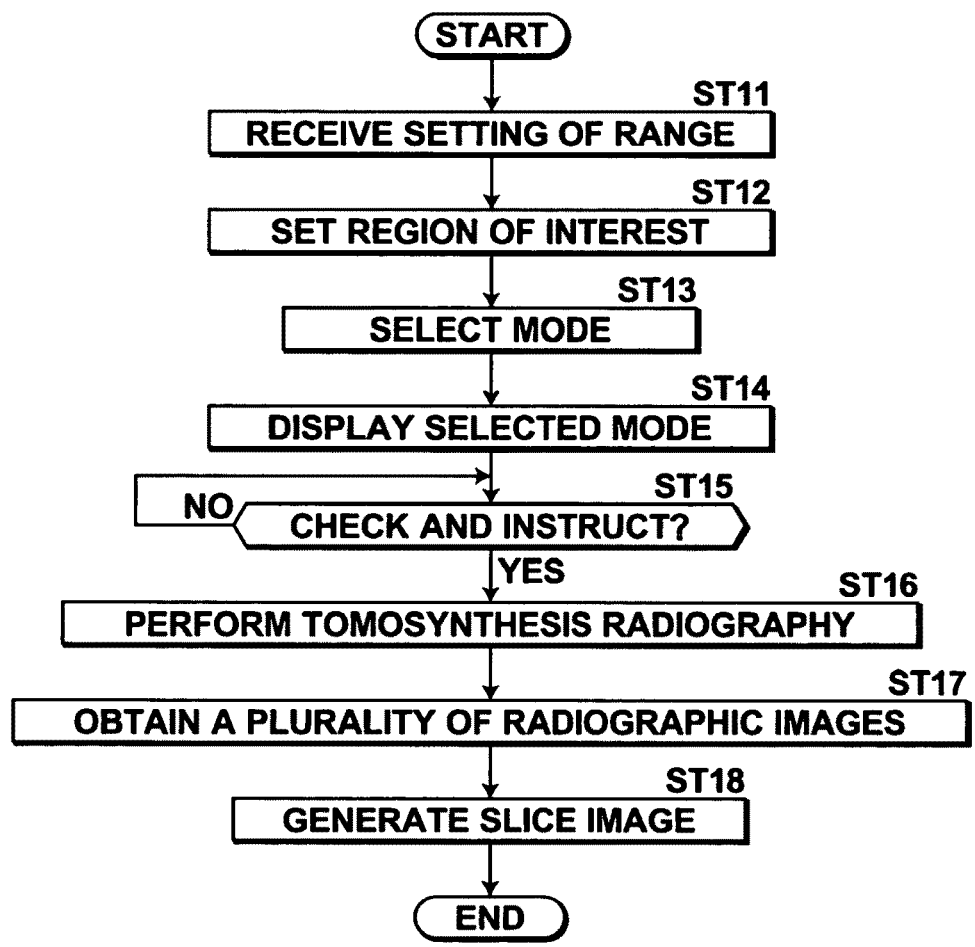
FIG. 8 is a flow chart of a process performed in a second embodiment.

Next, processing performed in the second embodiment will be described. FIG. 8 is a flow chart illustrating the processing performed in the second embodiment. First, the control unit 32 receives setting of the range with respect to the depth direction and the range with respect to the in-plane direction, which is perpendicular to the depth direction, by the operator from the operation unit 24 (receipt of range setting, step ST11). Next, the region-of-interest setting unit 30 sets a region of interest based on the ranges set by the operator (step ST12). The selection unit 28 selects the first mode or the second mode based on the region of interest (mode selection, step ST13). Meanwhile, the control unit 32 displays the selected mode at the display unit 25 (step ST14) to make the operator check the selected mode. The control unit 32 starts monitoring whether the operator has checked and instructed the mode (step ST15). If step ST15 is YES, tomosynthesis radiography is performed in the selected mode (step ST16), and the image obtainment unit 20 obtains a plurality of radiographic images (step ST17). Further, the reconstruction unit 22 reconstructs a slice image from the plurality of radiographic images (step ST18), and processing ends.

As described above, in the second embodiment, the first mode, in which only the X-ray tube 12 is moved, or the second mode, in which both of the X-ray tube 12 and the detector 14 are moved, is selected based on the region of interest. Therefore, it is possible to select the first mode or the second mode so that an appropriate slice image including the region of interest is obtained without imposing any burden on the operator.

Next, a third embodiment of the present invention will be described. An X-ray radiography apparatus in the third embodiment of the present invention is structured in the same manner as the X-ray radiography apparatus 10 according to the first embodiment, and only the processing performed in the apparatus of the third embodiment differs from the processing performed in the apparatus of the first embodiment. Therefore, detailed descriptions on the structure of the X-ray radiography apparatus 10 of the third embodiment are omitted. The X-ray radiography apparatus 10 of the third embodiment differs from the X-ray radiography apparatus 10 of the second embodiment, in that if the set region of interest is not included in the reconstructable region in the second mode in the second embodiment, a third mode is further selected in the third embodiment.

Figure 9:
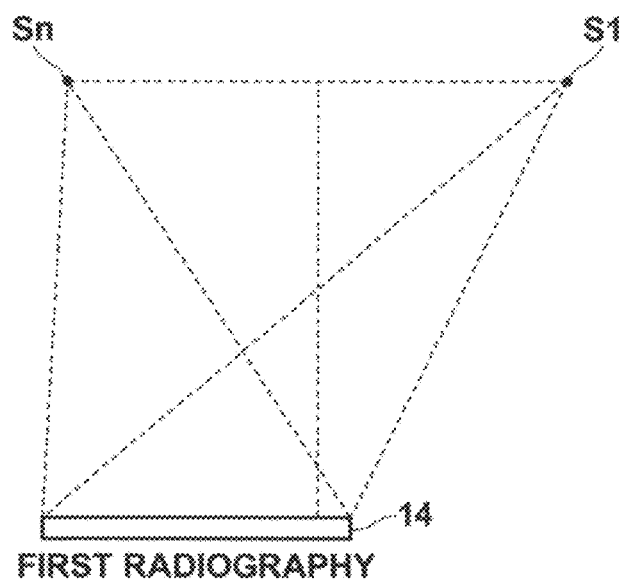
FIG. 9 is a diagram for explaining a third mode (No. 1)
Figure 10:
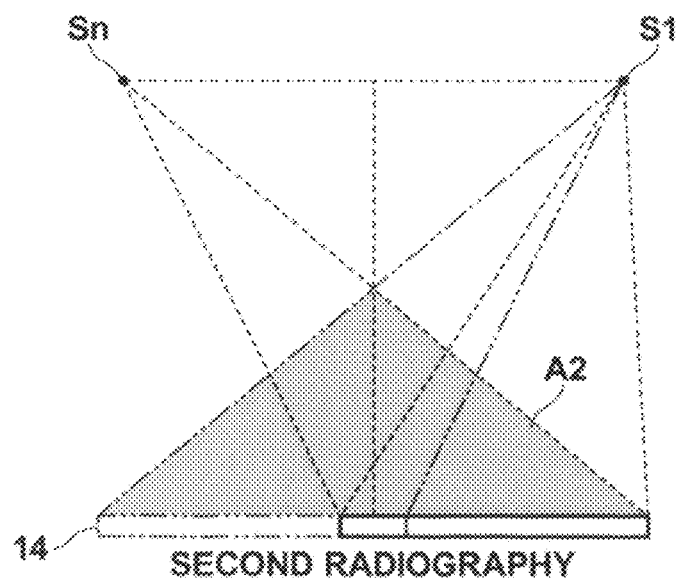
FIG. 10 is a diagram for explaining the third mode (No. 2).

In the third mode, the detector 14 is moved to a plurality of positions, and the detector 14 is fixed at each of the plurality of positions. Then, only the X-ray tube 12 is moved while the detector 14 is fixed at each of the positions. FIGS. 9 and 10 are diagrams for explaining the third mode. In FIGS. 9 and 10, the detector 14 is moved from a position to the other position, in other words, the detector 14 is moved to be located at two different positions. Needless to say, the detector 14 may be moved to be located at three or more different positions. In the third embodiment, the detector 14 is moved in such a manner that an edge of the detector 14 located at each position overlaps with an edge of the detector 14 located at the next position by a predetermined amount. First, in the first radiography illustrated in FIG. 9, the detector 14 is moved to a first position that is close to position Sn, and the detector 14 is fixed at the first position. While the detector 14 is fixed at the first position, the X-ray tube 12 is moved. The subject 2 is irradiated with X-rays while the X-ray tube 12 is moved. The X-rays that have passed through the subject 2 are detected by the detector 14 to obtain a plurality of radiographic images of the subject 2 when the X-ray tube 12 is located at respective positions during movement of the X-ray tube 12. Next, in the second radiography illustrated in FIG. 10, the detector 14 is moved to a second position that is close to position S1, and fixed at the second position. The subject 2 is irradiated with X-rays while the X-ray tube 12 is moved. The detector 14 detects X-rays that have passed through the subject 2 to obtain a plurality of radiographic images with the X-ray tube 12 located at respective positions during movement of the X-ray tube 12. In FIG. 10, X-rays output from the X-ray tube 12 that is located at position S1 to the detector 14 that is at the first position is indicated by an imaginary line.

In the third embodiment, with respect to the plurality of radiographic images obtained in the first and second radiography, the image obtainment unit 20 combines (connects) two radiographic images that are obtained when the X-ray tube 12 is located at the same position. In the first and second radiography, the detector 14 is moved in such a manner that the edges of the detector 14 overlap. Therefore, it is possible to easily combine two radiographic images obtained when the X-ray tube 12 is located at the same position. Further, the reconstruction unit 22 reconstructs a slice image from a plurality of combined radiographic images. In FIG. 10, a reconstructable area in the third embodiment is region A2, which is indicated in gray.

As described above, in the third embodiment, the detector 14 is moved to a plurality of positions. The detector 14 is fixed at each of the plurality of positions, and only the X-ray tube 12 is moved to perform tomosynthesis radiography. Therefore, it is possible to further increase the area of the reconstructable region, compared with the second mode, in which the X-ray tube 12 and the detector 14 are moved in a synchronized manner.

In the first through third embodiments, the first mode or the second mode is selected based on a body part to be radiographed or a region of interest, and the third mode is further selected. However, it is not necessary that the mode is selected based on the body part to be radiographed or the region of interest. The mode may be selected based on the purpose of examination using the obtained slice image (further examination, ordinary examination, observation of the course of a disease or the like), and radiography conditions, such as the kind of a lesion to be observed (calcification, a tumor or the like). For example, when the purpose of examination is observation of the course of the disease, it is possible to efficiently observe the course of the disease by selecting the same mode as the previous examination.

In the first and second embodiments, the first mode or the second mode is selected. Alternatively, one of the first through third modes may be selected.

In the first and second embodiments, tomosynthesis radiography is performed on a subject (patient) who is placed, in decubitus position, on the radiographic table. Needless to say, the present invention may be applied to tomosynthesis radiography using a radiographic table for standing position.

What is claimed is:

1. A radiography apparatus comprising:
a radiation source that outputs radiation to a subject;
a detector that detects the radiation that has passed through the subject;
an image obtainment unit that moves the radiation source and the detector relative to each other, thereby moving the radiation source to a plurality of positions, and that obtains a plurality of radiographic images of the subject by irradiating the subject with radiation from the plurality of positions;
an image reconstruction unit that reconstructs a slice image of the subject from the plurality of radiographic images;
a selection unit that selects, based on a condition of radiography, a first mode in which only the radiation source is moved or a second mode in which both of the radiation source and the detector are moved when the plurality of radiographic images are obtained, wherein the image obtainment unit obtains the plurality of radiographic images in the mode selected by the selection unit; and
a region-of-interest setting unit that sets a region of interest in the subject,
wherein the region of interest is a three-dimensional region defined by a range in the depth direction of the subject and a range in an in-plane direction of the subject, which is perpendicular to the depth direction, and
wherein the selection unit compares the region of interest that has been set by the region-of-interest setting unit with a reconstructable region in the first mode, selects the first mode if the region of interest that has been set by the region-of-interest setting unit is included in the reconstructable region in the first mode, and selects the second mode if the set region of interest is larger than the reconstructable region in the first mode.

2. A radiography apparatus, as defined in claim 1, wherein in the second mode, the radiation source and the detector are moved relative to each other in such a manner to be synchronized with each other.

3. A radiography apparatus, as defined in claim 1, wherein in the second mode, the detector is moved to a plurality of positions, and only the radiation source is moved while the detector is located at each of the plurality of positions.

* * * * *